(12) United States Patent
O'Halloran et al.

(10) Patent No.: US 7,262,301 B1
(45) Date of Patent: Aug. 28, 2007

(54) ZINC-CHELATING RATIOMETRIC FLUORESCENT PROBES AND RELATED METHODS

(75) Inventors: Thomas V. O'Halloran, Chicago, IL (US); Masayasu Taki, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/519,367

(22) Filed: Sep. 12, 2006

Related U.S. Application Data

(62) Division of application No. 10/887,465, filed on Jul. 8, 2004, now Pat. No. 7,105,680.

(60) Provisional application No. 60/485,587, filed on Jul. 8, 2003.

(51) Int. Cl.
*C07D 413/04* (2006.01)

(52) U.S. Cl. .................................................... 546/256
(58) Field of Classification Search ................ 546/256
See application file for complete search history.

(56) References Cited

U.S. PATENT DOCUMENTS 7,105,680 B1    9/2006    O'Halloran et al.

OTHER PUBLICATIONS

Taki, M; Wolford, JL; and O'Halloran, TV; Emission Ratiometric Imaging of Intracellular Zinc: Design of a Benzoxazole Fluorescent Sensor and Its Application in Two-Photon Microscopy, J. Am. Chem. Soc.., 2004, 712-713, 126.

Henry, MM and Fahrni, CJ; Excited State Intramolecular Proton Transfer and Metal Ion Complexation of 2-(2'-Hydroxyphenyl)benzazoles in Aqueous Solution; J. Phys. Chem. A, 2002, 5210-5220, vol. 106.

*Primary Examiner*—Patricia L. Morris
(74) *Attorney, Agent, or Firm*—Reinhart, Boerner, Van Deuren, S.C.

(57) ABSTRACT

Benzoxazole fluorescent sensor compounds and related ratiometric imaging methods for zinc metal ion.

1 Claim, 10 Drawing Sheets

Formula 1

Formula 6

Formula 2

Formula 7

Formula 3

Formula 8

Formula 4

Formula 9

Formula 5

Formula 10

FIGURE 6, continued
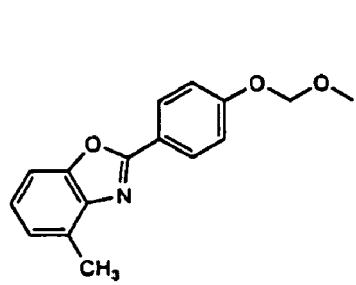
Formula 11
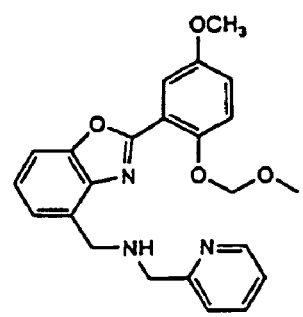
Formula 16
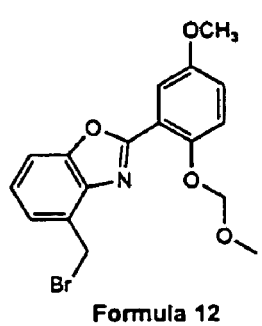
Formula 12
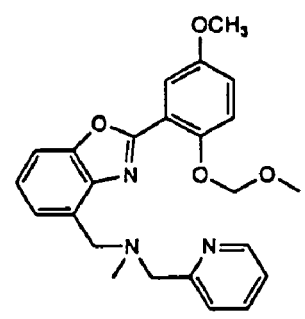
Formula 17
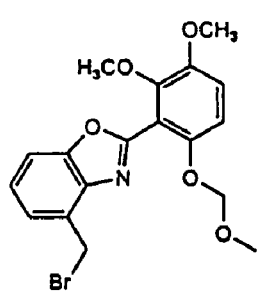
Formula 13
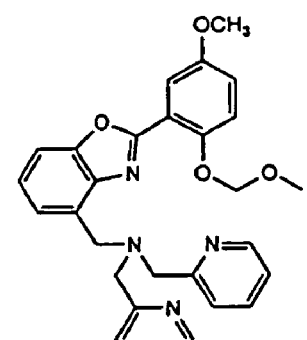
Formula 18
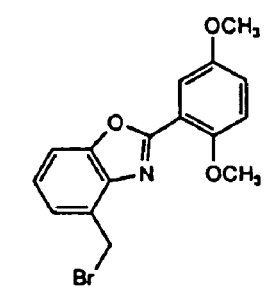
Formula 14
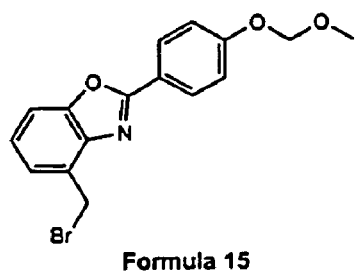
Formula 15
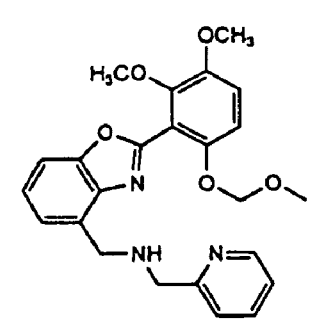
Formula 19

FIGURE 6, continued
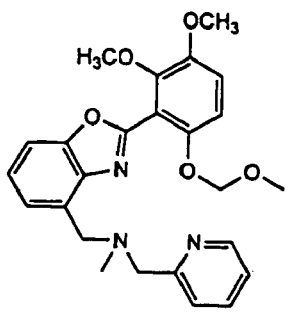
Formula 20
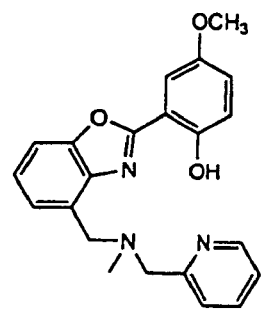
Formula 24
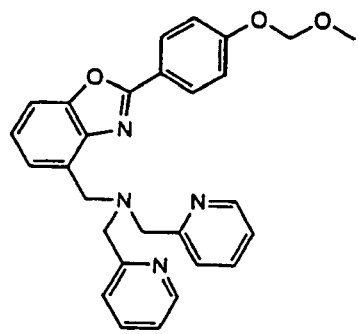
Formula 21
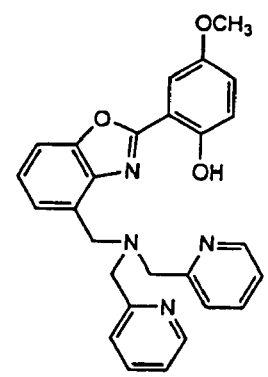
Formula 25
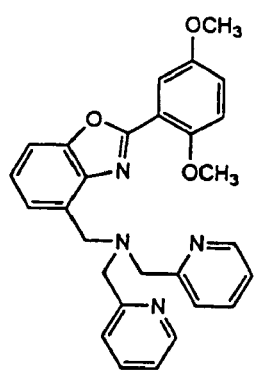
Formula 22
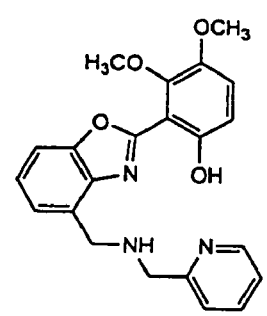
Formula 26
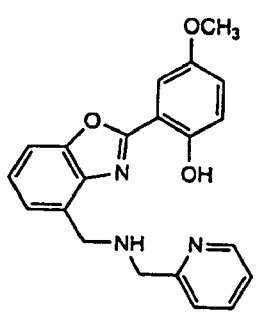
Formula 23
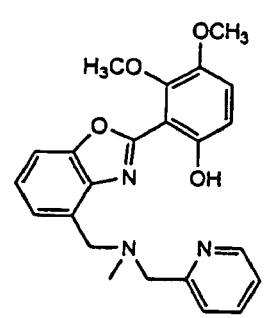
Formula 27

FIGURE 6, continued
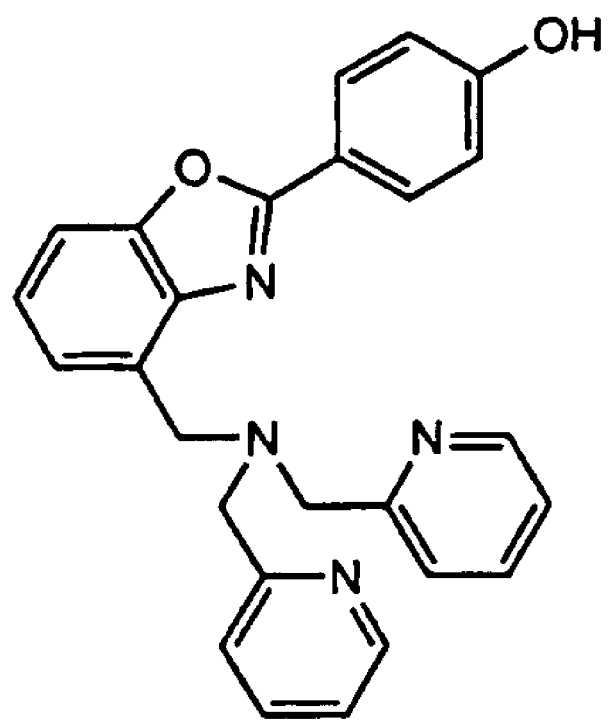
Formula 28

ZINC-CHELATING RATIOMETRIC FLUORESCENT PROBES AND RELATED METHODS

This application is a division of and claims priority benefit of prior application Ser. No. 10/887,465, filed Jul. 8, 2004 now U.S. Pat. No. 7,105,680, the entirety of which is incorporated herein by reference and which in turn claims priority benefit of provisional application No. 60/485,587, filed Jul. 8, 2003.

The United States government has certain rights to this invention pursuant to Grant Nos. DK52627 and GM38784 from the National Institutes of Health and the National Science Foundation, respectively, to Northwestern University.

BACKGROUND OF THE INVENTION

Zinc is an essential element in both enzymatic and biological systems, and is physiologically the second most abundant transition metal. The inorganic physiology of intracellular zinc is poorly understood but of emerging importance in understanding a variety of human disorders and disease states. Histochemical studies of mammalian tissues including the prostate, the insulin secreting beta cells of pancreatic islets, and the dentate neurons of the hippocampus reveal patterns of Zn(II) accumulation that are disrupted in some types of prostatic cancer, diabetes and neurodegerative disorders respectively. The function of zinc in these tissues or even within compartments of single cell organisms such as S. cerevease remains controversial.

In order to investigate the functions of such spectroscopically silent metal ions (e.g., $Ca^{2+}$ and $Zn^{+2}$) in biological systems, fluorescent sensor molecules that respond to a specific metal ion in the excitation or emission spectrum have shown to be useful tools. Several kinds of fluorescence probes for $Zn^{2+}$ that can be used under physiological condition have been reported to date, most of these utilize "on-off" fluorescent signaling system, in which fluorescence intensity increases lineally upon increasing $Zn^{2+}$ concentration. In these cases, however, the determination of the accurate $Zn^{2+}$ concentration in the cells should be impossible because the fluorescence intensity depends on many factors such as the cell thickness, incubation time, illumination intensity, dye concentration, and the photobleach of dye itself.

Confocal fluorescence microscopy has proved to be a central tool in understanding calcium biology and has the potential to resolve these issues in zinc biology. On the other hand, two-photon excitation (TPE) fluorescence microscopy provides significant advantages over standard laser confocal approaches by providing deeper sectioning, less phototoxicity and selective excitation of a smaller focal volume (i.e., femptoliter), thus decreasing background fluorescence. Such advances in instrumentation could be applied to the study of zinc physiology but would require the parallel development of new zinc-specific chemical probes that operate within cells.

Ratiometric probes that exhibit a large shift in the excitation and/or emission spectrum upon binding with the cation can minimize experimental error as the fluorescence intensity ratio between the apo form and the $Zn^{2+}$-bound form is dependent on only free $Zn^{2+}$ concentration. Recently, two ratiometric probes for $Zn^{2+}$ have been reported; however, as excitation probes, two different excitation wavelengths are needed for ratiometric cell imaging. As a result, this technique is not suitable for a confocal laser microscopy.

Such development has been an ongoing concern in the art. Protein-based zinc probes are useful in a variety of physiological experiments, but cannot be used without microinjection into each cell. Several benzofuran-based and coumazin probes have been used but only for excitation ratio imaging of a zinc loaded cell. Others in the art used 2-(2'-hydroxyphenyl)benzoxazole (HBO) as a fluorophore, which exhibits dual emission, utilizing ESIPT (Excited State Intramolecular Proton Transfer); however, intracellular analysis/imaging was not described. The search continues for a class of emission ratiometric probes for intracellular zinc, especially those with utility in two-photon fluorescence microscopy of mammalian cells.

SUMMARY OF THE INVENTION

Figure 1A:
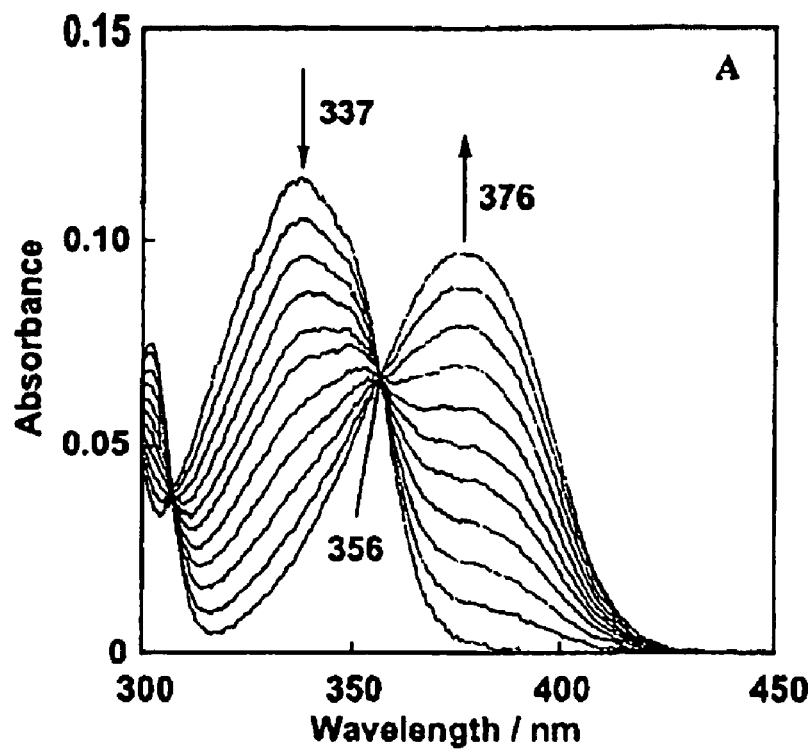
FIGS. 1A and 1B: (A) UV-vis spectral change observed upon the addition of $Zn^{2+}$ (0.5 µM each) to 5 µM of Zinbo-5 in 50 mM HEPES (pH 7.20, 0.1 M $KNO_3$) containing 5% DMSO. (B) Absorbance at 337 nm and 376 nm is plotted toward $[Zn^{2+}]_{total}/[Zinbo-5]$.

In light of the foregoing, it is an object of the present invention to provide a range of fluorescent sensor probe compounds and/or methods relating to ratiometric imaging of zinc ion, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide one or more benzoxazole compounds for use in ratiometric imaging applications, and to also quantitatively measure or assay zinc metal ion concentrations and changes thereof.

It is another object of the present invention to provide one or more benzoxazole compounds of the sort described herein substituted at a position on the fused ring to enhance zinc interaction, solvent solubility, cellular uptake and/or quantum yield.

It is another object of the present invention to provide a fluorescent sensor compound having a dissociation constant for zinc in the manomolar range, thereby allowing real time study of zinc physiology in living cells.

Other objects, features, benefits and advantages of the present invention will be apparent from this summary and descriptions of various embodiments, and will be readily apparent to those skilled in the art having knowledge of various zinc probes and analytic/imaging techniques. Such objects, features, benefits and advantages will be apparent from the above as taken into conjunction with the accompanying examples, data, figures and all reasonable inferences to be drawn therefrom.

Accordingly, in part, the present invention includes a compound of a formula

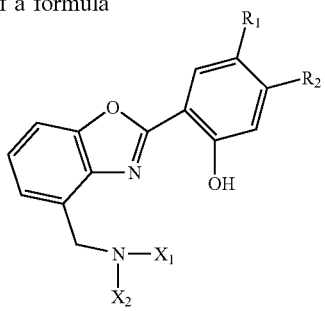

wherein $R_1$ and $R_2$ are independently selected from hydrogen, hydroxy, alkyl and alkoxy; and $X_1$ is (2-pyridinylalkyl); and $X_2$ is selected from hydrogen, alkyl, alkylhydroxy and (2-pyridinylalkyl). In certain embodiments, $X_2$ can be but is not limited to hydrogen, alkyl and (2-pyridinylalkyl) or as can be otherwise varied as would be understood by those skilled in the art to affect solvent solubility and/or cellular uptake. As described herein, such compounds can chelate, bind, complex or otherwise interact with zinc metal ions. As such, compounds of the present invention can be employed with a number of pharmaceutical and/or biological applications, including but not limited to zinc assays and zinc chelation in the treatment of various disease states.

Accordingly, the present invention also includes a composition comprising a $Zn^{+2}$ metal ion and one of the aforementioned compounds, but without limitation, a compound of a formula

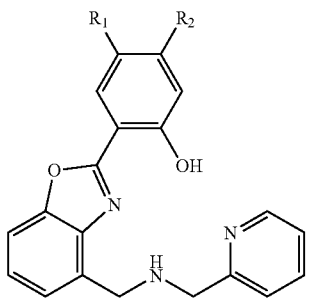

wherein $R_1$ and $R_2$ are as provided elsewhere herein. While the zinc ions may be found in an extracellular environment, such compositions comprising intracellular zinc ion can find application in one of the aforementioned assays or disease treatments.

In addition, such compounds can be used in conjunction with one or more methods for ratiometric imaging of intracellular $Zn^{+2}$ metal ion. Such a method comprises (1) providing a compound of the type described herein; (2) treating a mammalian cell with such a compound; and (3) irradiating the cell, then comparing fluorescent emissions of the compound unbound and bound with zinc. As would be understood by those skilled in the art, such imaging can be accomplished with a two-photon excitation laser, but can also be provided using various other spectroscopic techniques.

Likewise, a further departure from the prior art, the present invention also provides a method of using a polydentate benzoxazole compound to assay or measure $Zn^{+2}$ metal ion. Such a method comprises (1) providing a polydentate benzoxazole compound of the sort described herein, substituted at the 4-position of fused ring system; and (2) irradiating the compound in the presence of the metal ion, whether intracellular or extracellular, and comparing a ratio of fluorescence emission intensities. Plotting such a ratio against a standard concentration curve can be used to determine zinc concentrations and/or changes thereto, whether intracellular or extracellular.

One such fluorescent sensor compound—referred to as Zinbo-5, herein—illustrates various aspects of this invention: it is cell permeable, binds free $Zn^{2+}$ with a $K_d$ in the nanomolar range, and shows significant zinc-induced changes in quantum yield and in both the excitation and emission maxima. Compounds of this invention, such as Zinbo-5, are well suited for two-photon emission ratio microscopy and readily reveal changes in intracellular zinc within single cells. Such compounds and related methods can be applied to real time studies of zinc physiology in living cells.

The compounds of this invention can be characterized by a highly fluorescent benzoxazole core substituted with a variety of Zn-chelating groups pendent thereto. The synthesis of one such compound, Zinbo-5, which employs the aminomethylpyridine moiety, involves reaction of a MOM-protected phenol aldehyde derivative with amino-m-cresol and oxidation of the product with barium manganate to provide the benzoxazole derivative. Bromination of the methyl group using NBS, coupling with 2-aminomethylpyridine, and deprotection by p-toluene sulfonic acid yielded the compound referred herein as Zinbo-5. (A more detailed synthesis is provided in the following examples.)

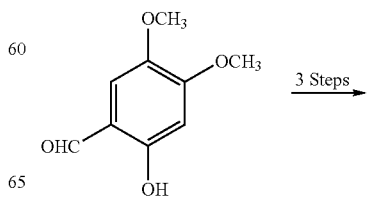

-continued

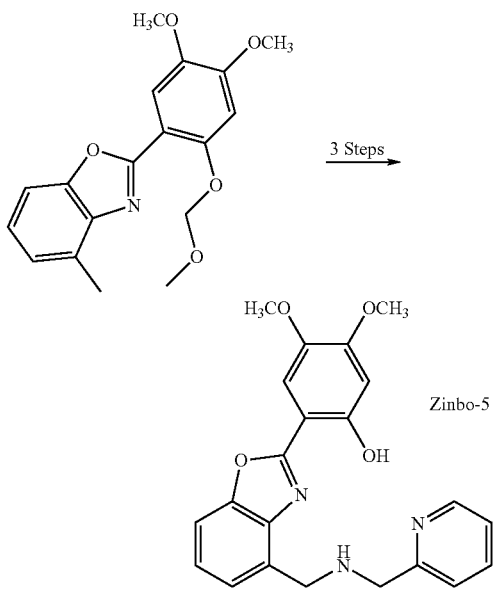

Other such benzoxazole compounds, with a range of substituted hydroxyphenyl moieties and/or various substitutions pendent to the heterocyclic core, can be prepared using synthetic procedures of the type described herein or straightforward modifications thereof—as needed to effect the desired structural variation(s).

EXAMPLES OF THE INVENTION

The following non-limiting examples and data illustrate various aspects and features relating to the compounds, compositions and/or methods of the present invention, including the use of the benzoxazole sensors of this invention, as are available through the synthetic methods described herein. In comparison with the prior art, the present compounds, compositions and/or methods provide results and data which are surprising, unexpected and contrary thereto. While the utility of this invention is illustrated through the use of several compounds and imaging techniques, it will be understood by those skilled in the art that comparable results are obtainable with various other compounds and methodologies, as are commensurate with the scope of this invention.

Example 1a

Synthesis of Zinbo-5

With reference to Scheme 1, below, the following material and reagents were used in preparation of compound Zinbo-5: 2,4,5-trimethoxybenzaldehyde (Aldrich, 98%), boron trichloride (Aldrich, 1.0 M solution in $CH_2Cl_2$), chloromethyl methyl ether (Aldrich, tech), 2-amino-m-cresol (Aldrich, 96%), N-bromosuccinimide (Aldrich, 99%), 2-(aminomethyl)pyridine (Aldrich, 99%). NMR: δ in ppm vs $SiMe_4$ (0 ppm, $^1H$, 400 MHz or 500 MHz), $CDCl_3$ (77.0 ppm, $^{13}C$, 500 MHz). Column chromatography: Merck silica gel (70-230 mesh). TLC: 0.25 mm, Merck silica gel 60 F254, visualizing at 254 mm.

Exhibit 1b 4,5-dimethoxy-2-hydroxybenzaldehyde (2)

A solution of boron trichloride (50 mL, 1.0 M solution in $CH_2Cl_2$) was slowly added to a solution of 2,4,5-trimethoxybenzaldehyde (3.92 g, 20 mmol) in $CH_2Cl_2$ (200 mL) at −78° C. (dry ice/acetone bath). The mixture was warmed to room temperature and stirred for three hours. 10 mL of HCl (37%) aqueous solution was poured into the resulting solution at 0° C. and extracted with $CH_2Cl_2$ (150 mL×3). The combined organic layer was washed with saturated aqueous NaCl (200 mL×2), water (100 mL×1), dried over $MgSO_4$, and evaporated to afford 3.72 g of a light brown solid (3.72 g, 99%): $^1H$-NMR (400 MHz, $CDCl_3$) δ3.88 (s, 3H), 3.94 (s, 3H), 6.47 (s, 1H), 6.91 (s, 1H), 9.70 (s, 1H).

Example 1c 4,5-dimethoxy-2-methoxymethoxybenzaldehyde (3)

Chloromethyl methyl ether (1.61 g, 20 mmol) at 0° C. was added to a solution of 1 (1.75 g, 14.9 mmol) and diisopropylethylamine (3.5 mL, 20 mmol) in $CH_2Cl_2$ (30 mL) was added, and the mixture was stirred for 15 hours at room temperature. Then water was added to the solution and the aqueous layer was extracted with $CH_2Cl_2$ (100 mL×3). The combined organic layer was washed with saturated aqueous NaCl (100 mL×2) followed by water (100 mL×1), dried over $MgSO_4$, and evaporated to afford 3.56 g of brown oil (2.56 g, 76%): $^1H$-NMR (500 MHz, $CDCl_3$) δ3.55 (s, 3H), 3.89 (s, 3H), 3.95 (s, 3H), 5.26 (s, 2H), 6.77 (s, 1H), 7.32 (s, 1H), 10.35 (s, 1H).

Example 1d 2-(4,5-dimethoxy-2-methoxymethoxyphenyl)-4-methylbenzoxazole (5)

A solution of 3 (2.26 g, 10 mmol) and 2-amino-m-cresol (1.23 g, 10 mmol) in benzene (70 mL) was refluxed for 15 hours using an additional funnel to remove water. The reaction mixture was cooled to room temperature and the solvent was removed in vacuo to afford the Schiff base compound 4 as a dark orange solid, which was used for the next reaction without further purification.

A solution of 4 (3.31 g, 10 mmol) and $BaMnO_4$ (10.3 g, 40 mmol) in benzene (70 mL) was refluxed for 5 hours under a flow of dry $N_2$ gas. After the reaction mixture was cooled to room temperature, $BaMnO_4$ was removed through Celite and the filtrate was concentrated in vacuo. The black residue was purified by silica gel column chromatography ($CHCl_3$) to afford 2.07 g of a pale yellow solid, 5 (2.07 g, 62%): $^1H$-NMR (400 MHz, $CDCl_3$) δ2.66 (s, 3H), 3.58 (s, 3H), 3.95 (s, 3H), 3.97 (s, 3H), 5.28 (s, 2H), 6.84 (s, 1H), 7.12 (d, 1H, J=8.0 Hz), 7.21 (t, 1H, J=8.0 Hz), 7.39 (d, 1H, J=8.0 Hz), 7.63 (s, 1H).

Example 1e 4-bromomethyl-2-(4,5-dimethoxy-2-methoxymethoxyphenyl)benzoxazole (6)

A mixture of 5 (1.39 g, 4.23 mmol), N-bromosuccinimide (0.75 g, 4.23 mmol) and AIBN (33 mg, 0.2 mmol) in $CCl_4$ (70 mL) was refluxed for 15 hours under a flow of dry $N_2$ gas. The reaction mixture was cooled to 0° C. and the precipitate was removed by filtration while maintaining the temperature at 0° C. After the solvent was evaporated, the residue was washed with small amount of ethanol several times to afford a pinkish solid 6 (1.14 g, 66%): $^1$H-NMR (500 MHz, CDCl$_3$) δ3.60 (s, 3H), 3.97 (s, 3H), 3.99 (s, 3H), 4.96 (s, 2H), 5.31 (s, 2H), 6.85 (s, 1H), 7.30 (t, 1H, J=8.0 Hz), 7.40 (d, 1H, J=8.0 Hz), 7.51 (d, 1H, J=8.0 Hz), 7.66 (s, 1H).

Example 1f 2-(4,5-dimethoxy-2-methoxymethoxyphenyl)-4-(2-pyridylmethyl)aminomethyl benzoxazole (7)

A mixture of 6 (612 mg, 1.5 mmol), 2-(aminomethyl) pyridine (1.08 g, 10 mmol), and Na$_2$CO$_3$ (excess) in CH$_3$CN (30 mL) was stirred overnight at room temperature. Insoluble material was removed by filtration and the filtrate was concentrated in vacuo. Water (20 mL) was added to the residue, which was extracted with ethyl acetate (20 mL) three times. The combined organic layer was washed with brine and water, dried over MgSO$_4$, and evaporated. The resulting oily material was purified by silica gel column chromatography (CHCl$_3$-ethyl acetate) to afford 7 as pale yellow oil (112 mg, 17%): $^1$H-NMR (500 MHz, CDCl$_3$) δ3.56 (s, 3H), 3.95 (s, 3H), 3.97 (s, 3H), 4.02 (s, 2H), 4.30 (s, 2H), 5.27 (s, 2H), 6.85 (s, 1H), 7.15 (dd, 1H, J=7.5, 5.0 Hz), 7.28 (t, 1H, J=7.5 Hz), 7.33 (d, 1H, J=7.5 Hz), 7.42 (d, 1H, J=7.5 Hz), 7.47 (d, 1H, J=7.5 Hz), 7.64 (m, 2H), 8.55 (d, 1H, J=5.0 Hz).

Example 1g 2-(4,5-dimethoxy-2-hydroxyphenyl)-4-(2-pyridlm-ethyl)aminomethylbenzoxazole (Zinbo-5)

A mixture of 7 (100 mg, 0.23 mmol) and p-toluene-sulfonic acid monohydrate (190 mg, 1 mmol) in methanol (20 mL) was stirred overnight at room temperature. After the solvent was evaporated, ethyl acetate (20 mL) was added to the resulting residue which was neutralized by Na$_2$CO$_3$, washed with brine and water, dried over MgSO$_4$, and concentrated in vacuo to give a pale yellow solid that was purified by silica gel column chromatography (ethyl acetate) and crystallized from ethanol to afford a white solid of Zinbo-5 (80 mg, 89%): $^1$H-NMR (500 MHz, CDCl$_3$) δ3.95 (s, 3H), 3.96 (s, 3H), 4.01 (s, 2H), 4.21 (s, 2H), 6.66 (s, 1H), 7.17 (dd, 1H, J=7.5, 5.0 Hz), 7.31 (t, 1H, J=8.0 Hz), 7.37-7.40 (m, 2H), 7.41 (s, 1H), 7.48 (d, 1H, J=8.0 Hz), 7.67 (t, 1H, J=7.5 Hz), 8.66 (d, 2H, J=5.0 Hz), 11.27 (s, 1H); Anal. Calcd for C$_{22}$H$_{21}$N$_3$O$_4$: C, 67.51; H, 5.41; N, 10.74. Found: C, 67.12; H, 5.25; N, 10.57.

Scheme S1

Scheme S1

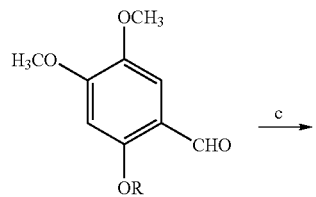

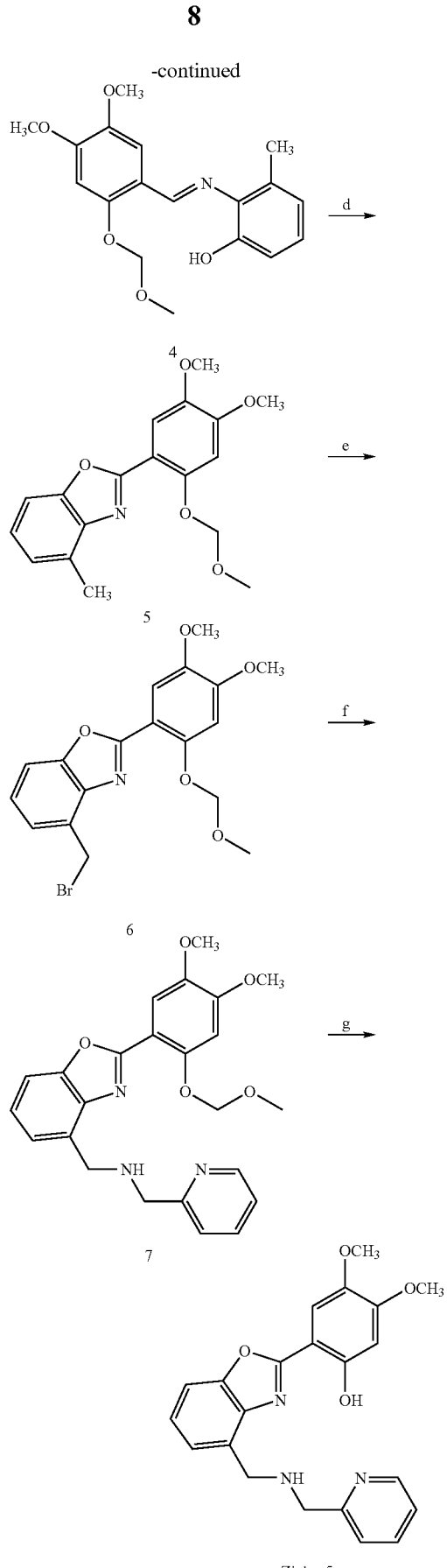

(a) BBr$_3$ in CH$_2$Cl$_2$, rt (b) CH$_2$OCH$_2$Cl, TEA in CH$_2$Cl$_2$, rt (c) amino-m-cresol in benzene, reflux (d) BaMnO$_4$ in benzene, reflux (e) NBS, AIBN in CCl$_4$, reflux (f) 2-aminomethylpyridine derivative, K$_2$CO$_3$ in CH$_3$CN, rt (g) TsOH in CH$_3$OH, rt.

Example 2

UV Visible and Fluorescence Spectroscopy

The UV absorption spectra of Zinbo-5 were recorded on a Hewlett-Packard 8453 spectrometer. Fluorescence spectra were recorded using a PTI fluorimeter (Photon Technology International). To reduce fluctuations of the excitation intensity during measurement, the lamp was turned on for 1 hour prior to the experiment. The path length was 1 cm with a cell volume of 3.0 mL. Quantum yields were determined to be 0.02 for the apo form and 0.10 for the zinc complex using fluorescein in 0.1 N NaOH ($\Phi$=0.95).[1]

Example 3a

Binding Constant Determination

A series of HEPES (2-[4-(2-hydroxyethyl)-1-piperazinyl]ethanesulfonic acid) buffer solutions (50 mM, pH 7.20, 0.1 M KNO$_3$) containing various amounts of ZnSO$_4$ (0~9.5 mM) and 10 mM of EGTA (ethylenebis(oxyethylenenitrilo) tetraacetic acid) were prepared. The concentration of free Zn$^{2+}$ was calculated with [EGTA]$_{total}$, [Zn$^{2+}$]$_{total}$, and K'$_{Zn-EGTA}$, the apparent binding constant at a given pH and ionic strength. K'$_{Zn-EGTA}$ value was calculated from Eq. 1 at pH=7.20

$$K'_{Zn-EGTA} = K_{(ZnL)}(1+10^{(pK_{LMH}-pH)})/((1+10^{(pH-pK_{Zn})})(1+10^{(pK_1-pH)}+10^{(pK_1+pK_2-2pH)})) \quad (Eq.\ 1)$$

using the following published pK and log K values for EGTA; pK$_1$=9.40, pK$_2$=8.79, pK$_3$=2.70, pK$_3$=2.70, pK$_{LMH}$=9.40, log K$_{(ZnL)}$=12.6 (25° C., μ=0.1 M).[2] All protonation constants were corrected upward by 0.11 when working in 0.1 M ionic strength. Thus, K'$_{ZN-EGTA}$ value at pH 7.20, 0.1 M ionic strength is 3.80×10$^8$ M$^{-1}$.

The calculated [ZN$^{2+}$]$_{free}$ concentration of each solution is:

| [Zn$^{2+}$]$^{total}$ (mM) | 0.5 | 1 | 2 | 3 | 4 | 5 | 6 | 7 | 8 | 9 |
|---|---|---|---|---|---|---|---|---|---|---|
| [Zn$^{2+}$]$^{free}$ (nM) | 0.14 | 0.29 | 0.66 | 1.1 | 1.8 | 2.6 | 4.0 | 6.1 | 11 | 24 |

The ratio between 395 nm and 443 nm intensities in the emission spectrum of each solution was measured with the excitation wavelength at 356 nm and was fitted to the following equation (Eq. 2).

$$R = (R_{min}K_d + R_{max}[Zn^{2+}])/(K_d + [Zn^{2+}]) \quad (Eq.\ 2)$$

Example 3b

Figure 1B:
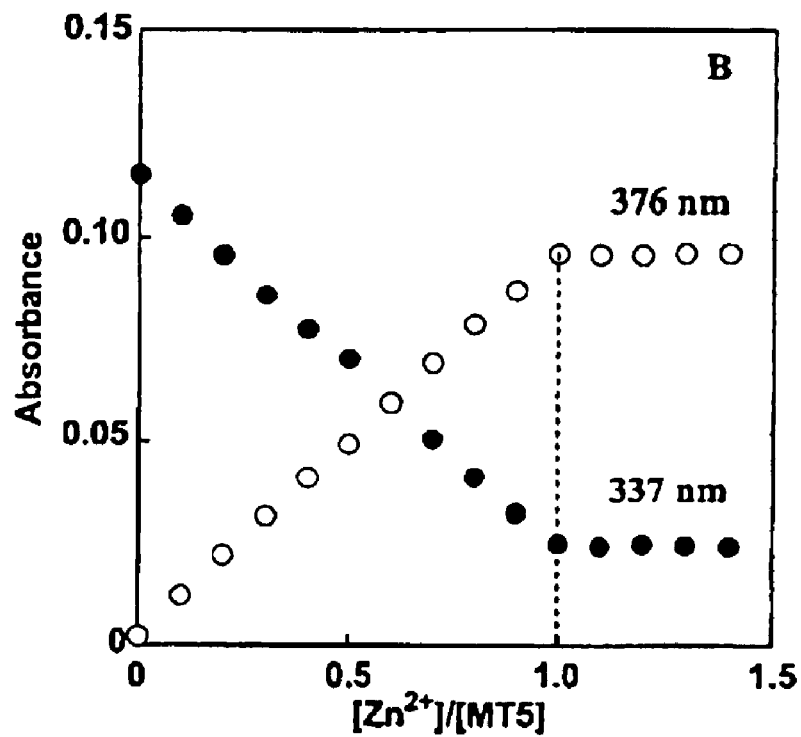

A mixture of aqueous buffer (50 mM HEPES, pH 7.20, 0.1 M KNO$_3$) and DMSO (5%, v/v) was used for the UV titration of Zinbo-5 with Zn$^{2+}$. A significant decrease in the absorption band of the apo at 337 nm and an increase of a new band at 376 nm was observed with a distinct isosbestic point at 356 nm (FIG. 1A). The absorption bands at 337 nm and 376 nm linearly decreased and increased, respectively, up to a 1:1 [Zn$^{2+}$]/[Zinbo-5] ratio, indicating formation of a 1:1 complex (FIG. 1B).

Example 3c

Figure 2:
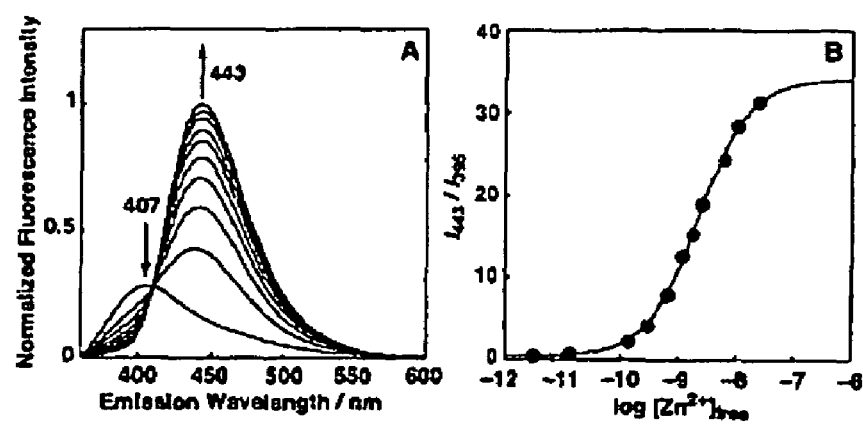
FIG. 2. (A) Emission spectra of Zinbo-5 with the excitation at 356 nm in $Zn^{2+}$/EGTA buffered system (50 mM HEPES, pH 7.20, 0.1 M $KNO_3$; 10 mM EGTA, 1-9 mM zinc sulfate) at 0, 0.14, 0.29, 0.66, 1.1, 1.8, 2.6, 4.0, 6.1, and 11 nM free $Zn^{2+}$, respectively. (B) Plots of the fluorescence intensity ratio between 395 nm and 443 nm ($I_{443}/I_{395}$) with a best curve for a dissociation constant of $2.1\pm0.1\times10^{-9}$.

FIG. 2A shows the emission spectra of Zinbo-5 when excited at 356 nm, which is the isosbestic point of the absorption titration spectrum at various free Zn$^{2+}$ concentrations. The apo form exhibits a characteristic band at 407 nm that shifts to 443 nm upon binding with Zn$^{2+}$. Comparisons within the Zinbo family indicate that the 4-hydroxyl function gives rise to a larger shift relative to the unsubstituted forms (data not shown). In contrast to those model compounds which exhibit a blue shift in emission upon zinc binding, Zn$^{2+}$ binding to Zinbo-5 leads to a red shift in the emission, suggesting a different photophysical mechanism for the polydentate complexes of this invention.

Example 3d

Figure 3:
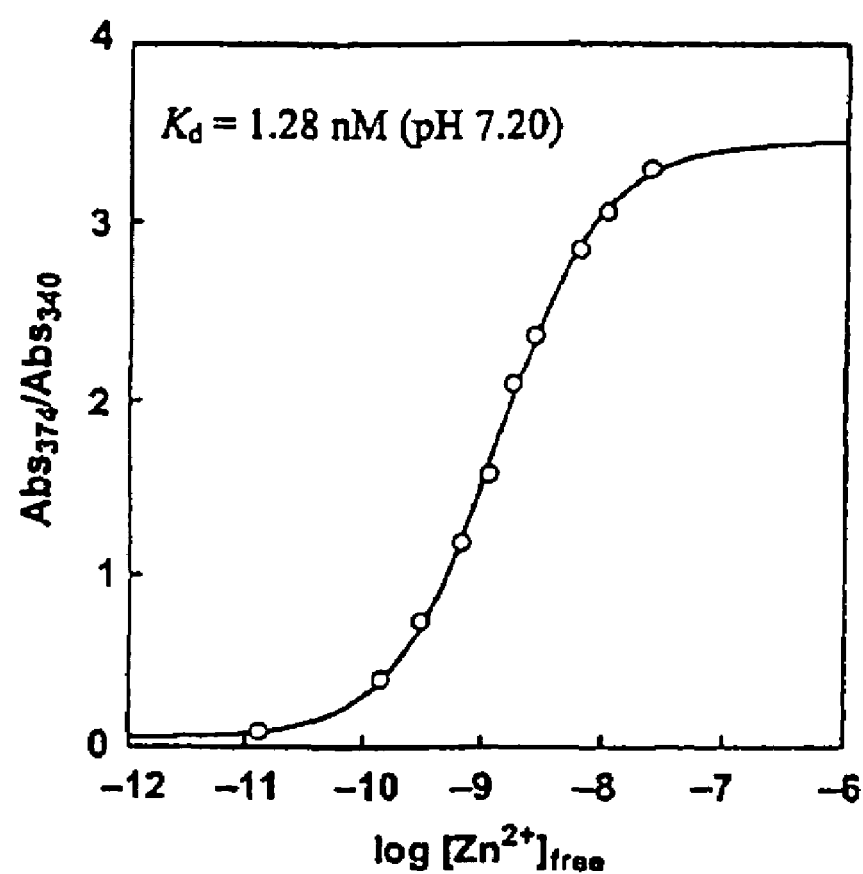
FIG. 3. UV determination of dissociation constant, $K_d$: (A) Absorption ratio between at 340 nm and at 374 nm ($Abs_{374}/Abs_{340}$) in $Zn^{2+}$-buffered solution (50 mM HEPES, pH 7.20, 0.1 M $KNO_3$; 10 nM EGTA, 1-9 mM zinc sulfate).

The apparent dissociation constant (K$_d$=2.2±0.1 nM at pH 7.20) for Zn$^{2+}$ was determined by plotting (FIG. 2B) the fluorescence intensity ratio between 395 nm and 443 nm (or UV absorbance as shown in FIG. 3) against log[Zn$^{2+}$]$_{free}$ and fitting this data as described in the literature. The corresponding pZn value (–log[Zn$^{2+}$], where [Zn$^{2+}$] is the free metal concentration calculated for an aqueous solution containing 10 mM ligand and 1 mM zinc ion at pH 7.20 and 0.1 M ionic strength) is 9.3. Such results are comparable to the affinity of prior art Zinquin, Zinpyr and ZnAF probes (Table 1), below, which have been used in studies of zinc-loaded cells. The Zn$^{2+}$ affinity of Zinbo-5 is much higher than that of di(2-picolyl)amine (DPA), indicating—without limitation—that the phenolate oxygen and benoxazole nitrogen are likely chelating the metal as the third and fourth ligands.

TABLE 1

Calculated pZn Values (-log[Zn]$_{free}$) for a Solution Containing 10 μM of the Indicated Ligand, 1 μM of Zn(II) at pH 7.20, 0.1 M Ionic Strength, and 25° C.

| Ligand | pZn |
|---|---|
| NTA | 9.0 |
| EGTA | 9.5 |
| EDTA | 14.3 |
| Zinpyr-1[a] | 10.1 |
| Zinpyr-4[c] | 10.1 |
| ZnAF-2[d] | 9.5 |
| ZnAF-R2[e] | 9.5 |
| Zinbo-5 | 9.3 |
| TPEN | 16.0 |
| Zinquin acid | 9.3 |
| carbonic anhydrase | 12.4 |
| Zinpyr-2[b] | 10.3 |
| ZnAF-1[d] | 10.1 |
| ZnAF-R1[e] | 10.1 |
| L$^3$[f] | 10.8 |

[a]Walkup, G. K.; Burdette, S. C.; Lippard, S. J.; Tsien, R. Y. J Am Chem Soc 2000, 122, 5644-5645.
[b]Burdette, S. C.; Walkup, G. K.; Spingler, B.; Tsien, R. Y.; Lippard, S. J. J A Chem Soc 2001, 123, 7831-7841.
[c]Burdette, S. C.; Frederickson, C. J.; Bu, W., and Lippard, S. J. J Am Chem Soc 2003, 125, 1778-1787.
[d]Hirano, T.; Kikuchi, K.; Urano, Y.; Higuchi, T.; Nagano, T. J Am Chem Soc 2000, 122, 12399-12400.
[e]Maruyama, S.; Kikuchi, K.; Hirano, T.; Urano, Y.; Nagano, T. J Am Chem Soc 2002, 124, 10650-10651.
[f]Koike, T.; Watanabe, T.; Aoki, S.; Kimura, E.; Shiro, M. J Am Chem Soc. 1996, 118, 12696-12703.

Example 4

Figure 4:
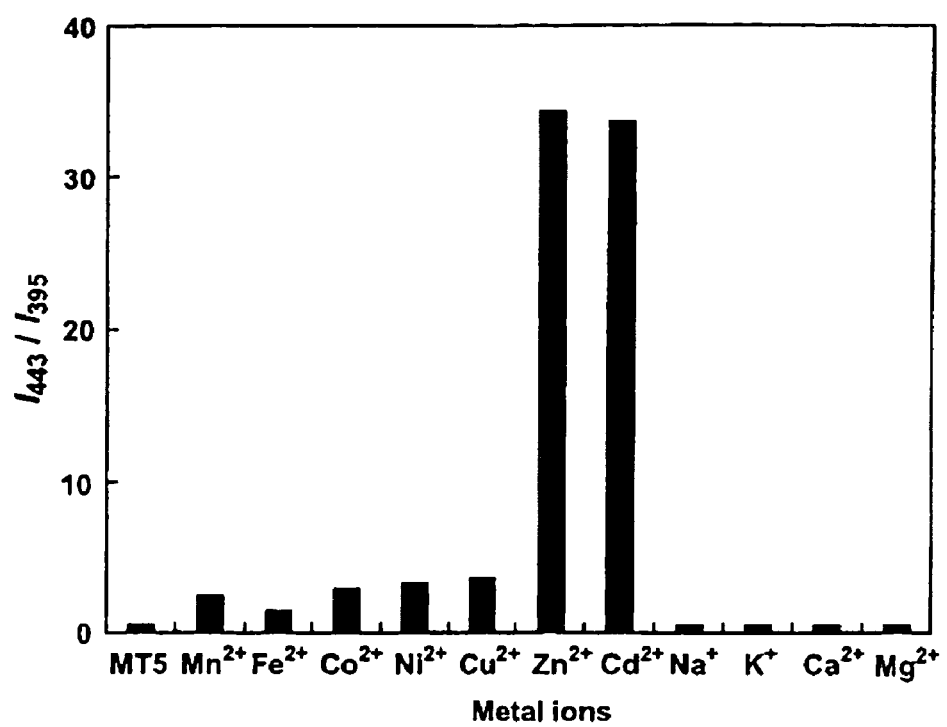
FIG. 4. Metal ion selectivity of Zinbo-5. Bars are a presentation of the fluorescence ratio $I_{443}/I_{395}$. Heavy metals (20 µM) and $Na^+$, $K^+$, $Ca^{2+}$, $Mg^{2+}$ (5 mM) were added to 1.5 µM Zinbo-5 in the presence of 10 µM EDTA.

A survey of Zinbo-5 fluorescence in a series of biological buffers containing physiologically relevant metal ions reveals that only $Zn^{2+}$ and $Cd^{2+}$ induced an emission shift as shown in FIG. 2A, whereas other heavy metal ions, $Mn^{2+}$, $Co^{2+}$, $Ni^{2+}$, $Fe^+$ and $Cu^{2+}$, quenched the fluorescence (FIG. 4). $Na^+$, $K^+$, $Ca^{2+}$ and $Mg^{2+}$ afforded no fluorescent response even at metal concentrations as high as 5 mM. Neither high nor low concentrations of alkali metal or alkaline earth metal ions altered the fluorescent response of Zinbo-5 to $Zn^{2+}$, suggesting that this probe may be useful in a wide range of biological and microscopic applications.

Example 5

Ratio Imaging Methods

The Zinbo-5 probe was tested in the mouse fibroblast LTK cell line. Cells were fixed, treated with a saturated solution of Zinbo-5 and then imaged with two-photon excitation (TPE) laser scanning microscopy using on Zeiss 510 LSM (upright configuration). The excitation beam produced by the femtosecond pulsed Ti:sapphire laser (Tsunami, Spectra-Physics; 8 W Millennia pump) was tuned to 710 nm, (pumping power 6.5 W with 0.5 W entering the Zeiss AOM) was passed through an LSM 510 microscope with an HFT 650 dichroic (Zeiss) and focused onto coverslip adherent fibroblasts using a 63x oil-immersion objective (Zeiss). The NLO META scan head (Zeiss) allowed data collection in 10.7 nm windows centered at 445 nm and 402 nm.

Figure 5:
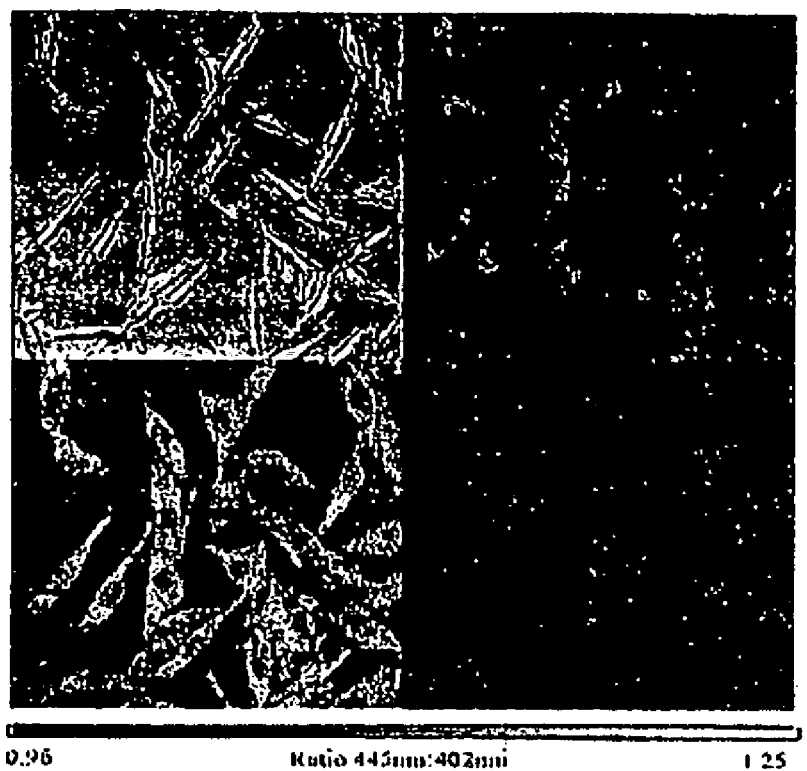
FIG. 5. Emission ratio images of fibroblast (LTK) cells treated with Zinbo-5. (A) Brightfield transmission image; (B) ratio image of the intensities at 445 nm and 402 nm; (C) ratio image following a 30 minute treatment with 10 µM zinc sulfate and 20 µM pyrithione at pH 7.4, 25° C., followed by wash with Zinbo-5 stock; (D) ratio image of the same field after a 15 minute treatment with 1 mM TPEN.

Cells were imaged in the presence of Zinbo-5 to provide the contrast of unbound dye outside of the cells (FIG. 5). After imaging, the same field of cells was treated with 10 µM zinc sulfate and 20 µM pyrithione, a zinc-selective ionophore, resulting in an anticipated increase in the intracellular ratio of emissions from 445 nm and 402 nm (FIG. 5, d-f). Finally, the intracellular ratio was made equal to that of the surrounding unbound dye by treating the same field of view with TPEN (FIG. 5, g-i). These data indicate that Zinbo-5 may be an excellent choice for a ratiometric zinc sensor in biological studies.

Example 6

Cell Culture

LTK cells were grown as previously published (Nasir, M. S., et al., JBIC (1999) 4:775-783). Cells grown on coverslips were fixed with 4% formaldehyde on ice for 20 minutes and washed with cold PBS before staining. The cells were stained on ice for 30 minutes in 2 mL of PBS and 4 µL of a 5 mM solution of Zinbo-5 in DMSO, thus in a saturated solution with a final Zinbo-5 concentration limited by the maximal water solubility of 1.5 µM. Coverslips were attached to slides using Secure-Seal spacers (Molecular Probes) with the saturated staining solution in the spacer well.

Example 7

Microscopy and Ratio Imaging

512×512 pixel images were obtained in the presence of Zinbo-5 using a Zeiss LSM 510 set to a frame scan speed of four and an average of four. META detection and Zeiss software (LSM 510, version 3.0; Carl Zeiss, Inc.) in lambda mode allowed detection and data collection in two 10.7 nm channels centered at 402 and 445 nm. Images collected in these two channels were evenly divided and then multiplied by 30 to improve contrast using the Zeiss software ratio function. Images were collected with a Plan-Apo 63x oil objective, 1.4 n.a. (Carl Zeiss, Inc.) at 25° C. (See FIG. 5A)

For cells grown in standard conditions, the ratio image suggests very low levels of available $Zn^{2+}$ (FIG. 5B). The ratio image changes in a manner dependent upon the availability of Zn(II) within the cell: the ratio is clearly higher when the intracellular Zn(II) is increased by addition of 10 µM zinc sulfate and 20 µM pyrithione, a zinc-chelating ionophore (FIG. 5C). This corresponds to an average intracellular increase in the ratio of ca. 15%. Next, the signals in these ratio images were shown to originate from $Zn^{2+}$/Zinbo-5 complex by treatment with a tighter binding competitor. Treatment of cells with an excess of the cell-permeable, high affinity zinc chelator, N,N,N',N'-tetrakis (2-pyridylmethyl) ethylenediamine (TPEN), decreases the intracellular ratio by 30% to equal that of the unbound probe (FIG. 5D). This and control experiments on untreated cells indicate that autofluorescence does not contribute to the ratio images under these conditions.

The emission ratio imaging studies and data of the preceding examples indicate that Zinbo-5 and other compounds and/or methods of this invention can readily reveal changes in intracellular or extracellular zinc availability. The photophysical data further suggest that the compounds of this invention can also be used in standard laser scanning confocal imaging or in epifluorescence excitation ratio imaging approaches to studying zinc in tissues and cells. Such methods are particularly amenable to investigation of live tissue samples in real time and are being applied to studies of the hippocampus, where physiological fluctuations in synaptic zinc concentration are estimated to be as high as 100-300 µM or as low 2 nM.[5]

Figure 6:
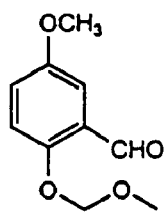
FIG. 6. Structural formulae of compounds and intermediates en route thereto, in accordance with this invention.
Figure 6:
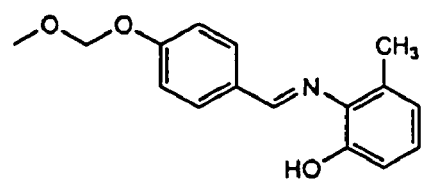
Figure 6:
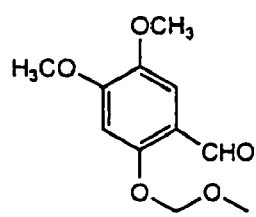
Figure 6:
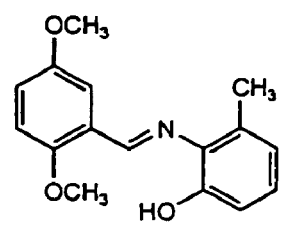
Figure 6:
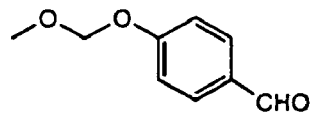
Figure 6:
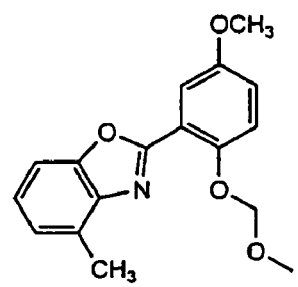
Figure 6:
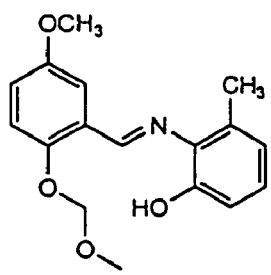
Figure 6:
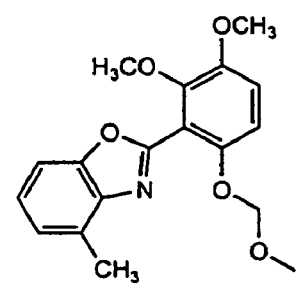
Figure 6:
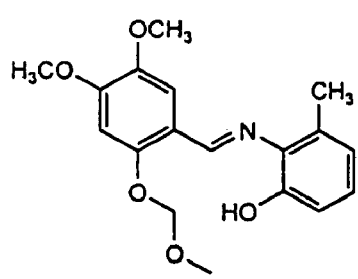
Figure 6:
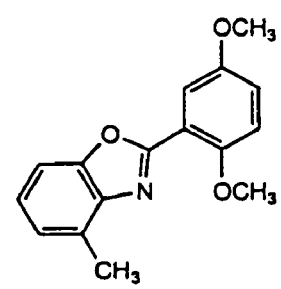
Figure 7:
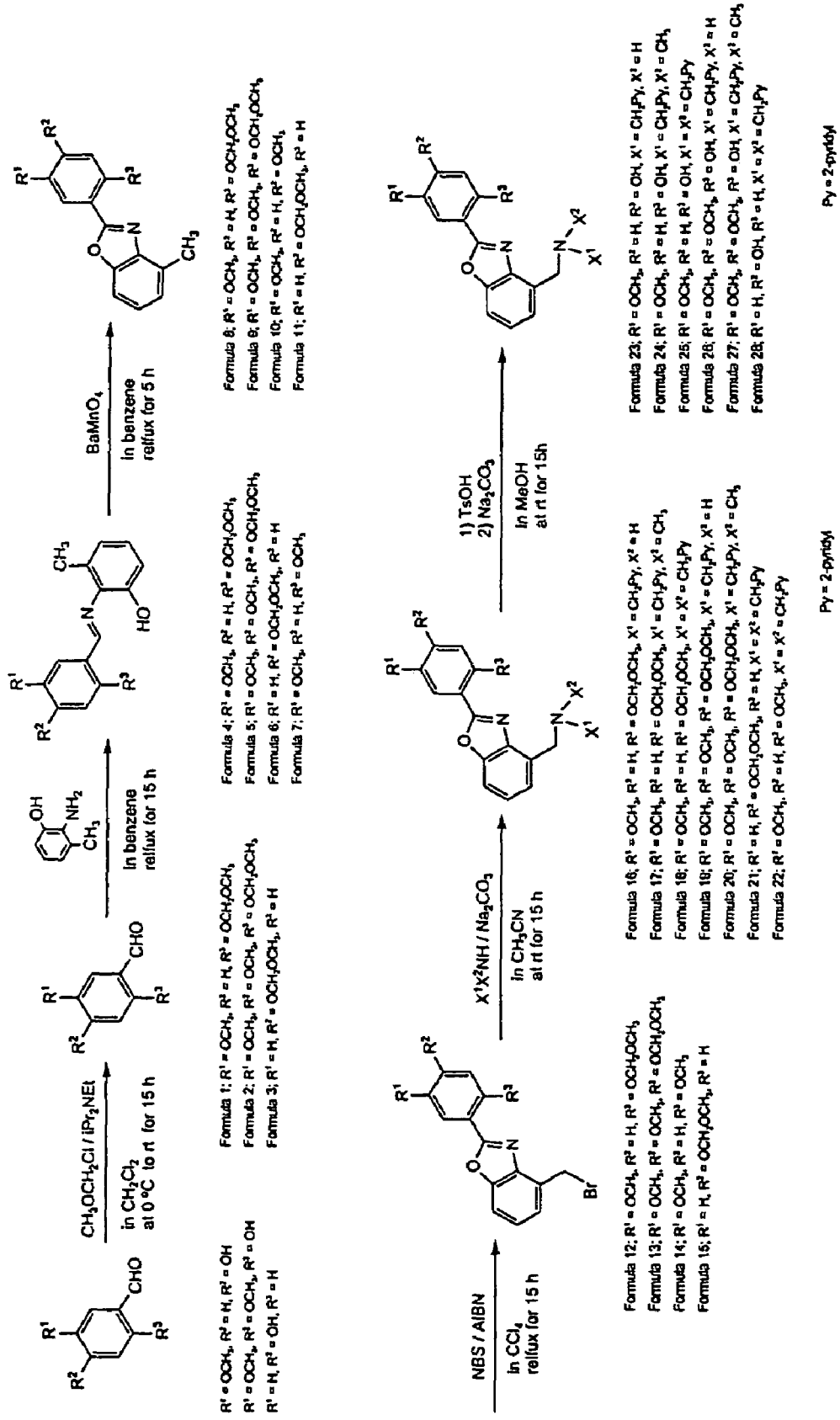
FIG. 7. A schematic representation of the synthesis of the compounds and intermediates represented by the structural formulae of FIG. 6.

In accordance with this invention, various other fluorescent probe compounds are available and can be used as described herein, as would be understood by those skilled in the art made aware of this invention. Without limitation, several such compounds and their respective synthetic intermediates (F1, F2, etc.) are prepared as described below, with reference to the structural formulae and schematics of FIGS. 6 and 7.

Example 8

Production of
5-methoxy-2-methoxymethoxybenzaldehyde (F1)

To a solution of 2-hydroxy-5-methoxybenzaldehyde (10 g, 67.5 mmol) and diisopropylethylamine (14 mL, 80 mmol) in $CH_2Cl_2$ (100 mL) was added chloromethyl methyl ether (6.1 mL, 80 mmol) at 0° C., and the mixture was stirred for 15 hours at room temperature. Then, water was added to the solution, the aqueous layer was extracted with $CH_2Cl_2$ (100 mL×3). The combined organic layer was washed with saturated aqueous NaCl (100 mL×2), water (100 mL×1), dried over $MgSO_4$, and evaporated to afford the objective compound as a brown oil (11.76 g, 91%), which was used for next reaction without further purification: $^1$H-NMR (400 MHz, $CDCl_3$) δ3.52 (s, 3H), 3.81 (s, 3H), 5.24 (s, 2H), 7.12 (dd, 1H, J=9.6, 3.2 Hz), 7.18(d, 1H, J=9.6 Hz), 7.32(d, 1H, J=3.2 Hz), 10.47 (s, 1H).

Example 9

Production of
4,5-dimethoxy-2-methoxymethoxybenzaldehyde (F2)

4,5-dimethoxy-2-methoxymethoxybenzaldehyde (F2) was prepared in a similar manner for the preparation of 5-methoxy-2-methoxymethoxybenzaldehyde (F1) by using 4,5-dimethoxy-2-hydroxybenzaldehyde (1.75 g, 14.9 mmol) instead of 2-hydroxy-5-methoxybenzaldehyde in 76% (2.56 g): $^1$H-NMR (500 MHz, CDCl$_3$) δ3.55 (s, 3H), 3.89 (s, 3H), 3.95 (s, 3H), 5.26 (s, 2H), 6.77 (s, 1H), 7.32 (s, 1H) 10.35 (s, 1H).

Example 10

Production of 4-methoxymethoxybenzaldehyde (F3)

4-methoxymethoxybenzaldehyde (F3) was prepared in a similar manner for the preparation of 5-methoxy-2-methoxymethoxybenzaldehyde (F1) by using 4-hydroxybenzaldehyde (4.48 g, 40 mmol) instead of 2-hydroxy-5-methoxybenzaldehyde in 96% (6.40 g): $^1$H-NMR (500 MHz, CDCl$_3$) δ3.53 (s, 1H), 5.24 (s, 2H), 7.17 (d, 1H, J=9.0 Hz), 7.35 (d, 1H, J=9.0 Hz), 10.52 (s, 1H).

Example 11

Production of 2-[(5-Methoxy-2-methoxymethoxybenzylidene)amino]-3-methylphenol (F4)

A solution of 5-methoxy-2-methoxymethoxybenzaldehyde (F1) (2.77 g, 16.5 mmol) and 2-amino-m-cresol (2.03 g, 16.5 mmol) in benzene (70 mL) was refluxed for 15 h using an additional funnel to remove water. After the reaction mixture was cooled to room temperature, the solvent was removed in vacuo and the resulting residue was washed with ethanol to afford the objective compound as a orange solid (84%), which was used for next reaction without further purification: $^1$H-NMR (400 MHz, DMSO-d$_6$) δ2.31 (s, 3H), 3.45 (s, 3H), 3.85 (s, 3H), 5.18 (s, 2H), 6.59 (s, 1H), 6.77 (d, 1H, J=8.0 Hz), 6.83 (d, 1H, J=8.0 Hz), 6.99 (t, 1H, J=8.0 Hz), 7.03 (dd, 1H, J=9.0, 2.5 Hz), 7.14 (d, 1H, J=9.0 Hz), 7.68 (s, 1H), 8.95 (s, 1H).

Example 12

Production of 2-[(4,5-dimethoxy-2-methoxymethoxybenzylidene)amino]-3-methylphenol (F5)

2-[(4,5-dimethoxy-2-methoxymethoxybenzylidene)amino]-3-methylphenol (F5) was prepared in a similar manner for the preparation of 2-[(5-Methoxy-2-methoxymethoxybenzylidene)amino]-3-methylphenol (F4) by using 4,5-dimethoxy-2-methoxymethoxybenzaldehyde (F2) (2.26 g, 10 mmol) instead of 5-methoxy-2-methoxymethoxybenzaldehyde (F1) in 86% (2.80 g): $^1$H-NMR (500 MHz, CDCl$_3$) δ3.53 (s, 3H), 5.24 (s, 3H), 7.17 (d, 1H, J=9.0 Hz), 7.35 (d, 1H, J=9.0 Hz), 10.52 (s, 1H).

Example 13

Production of 2-[(4-methoxymethoxybenzylidene)amino]-3-methylphenol (F6)

2-[(4-methoxymethoxybenzylidene)amino]-3-methylphenol (F6) was prepared in a similar manner for the preparation of 2-[(5-Methoxy-2-methoxymethoxybenzylidene)amino]-3-methylphenol (F4) by using 4-methoxymethoxybenzaldehyde (F3) (3.32 g, 20 mmol) instead of 5-methoxy-2-methoxymethoxybenzaldehyde (F1) in 84% (4.56 g): $^1$H-NMR (500 MHz, CDCl$_3$) δ3.53 (s, 3H), 5.24 (s, 3H), 7.17 (d, 1H, J=9.0 Hz), 7.35 (d, 1H, J=9.0 Hz), 10.52 (s, 1H).

Example 14

Production of 2-[(2,5-dimethoxybenzylidene)amino]-3-methylphenol (F7)

2-[(2,5-dimethoxybenzylidene)amino]-3-methylphenol (F7) was prepared in a similar manner for the preparation of 2-[(5-Methoxy-2-methoxymethoxybenzylidene)amino]-3-methylphenol (F4) by using 2,5-dimethoxybenzaldehyde (3.32 g, 20 mmol) instead of 5-methoxy-2-methoxymethoxybenzaldehyde (F1) in 82% (4.44 g): $^1$H-NMR (400 MHz, CDCl$_3$) δ2.32 (s, 3H), 3.84 (s, 6H), 6.77 (d, 1H, J=7.6 Hz), 6.82 (d, 1H, J=2.0 Hz), 6.83 (d, 1H, J=7.6 Hz), 6.91 (d, 1H, J=9.2 Hz), 6.99 (t, 1H, J=7.6 Hz), 7.06 (dd 1H, J=9.2, 2.0 Hz), 7.69 (s, 1H), 8.94 (s, 1H).

Example 15

Production of 2-(5-methoxy-2-methoxymethoxyphenyl)-4-methylbenzoxazole (F8)

A solution of 2-[(5-methoxy-2-methoxymethoxybenzylidene)amino]-3-methylphenol (F4) (1.51 g, 5 mmol) and BaMnO$_4$ (5.13 g, 20 mmol) in benzene (50 mL) was refluxed for 5 hours under dry N$_2$ gas flowing. After the reaction mixture was cooled to room temperature, BaMnO$_4$ was removed through Celite and the filtrate was concentrated in vacuo. The black residue was purified by silica gel column chromatography (CHCl$_3$) to afford the objective compound as a pale yellow solid (976 mg, 65%): $^1$H-NMR (500 MHz, CDCl$_3$) , 2.68 (s, 3H), 3.55 (s, 3H), 3.87 (s, 3H), 5.25 (s, 2H), 7.02 (dd, 1H, J=9.0, 3.0 Hz), 7.15 (d, 1H, J=8.0 Hz), 7.21 (d, 1H, J=9.0 Hz), 7.24 (t, 1H, J=8.0 Hz), 7.42 (d, 1H, J=8.0 Hz), 7.63 (d, 1H, J=3.0 Hz).

Example 16

Production of 2-(4,5-dimethoxy-2-methoxymethoxyphenyl)-4-methylbenzoxazole (F9)

2-(4,5-dimethoxy-2-methoxymethoxyphenyl)-4-methylbenzoxazole (F9) was prepared in a similar manner for the preparation of 2-(5-methoxy-2-methoxymethoxyphenyl)-4-methylbenzoxazole (F8) by using 2-[(4-methoxymethoxybenzylidene)amino]-3-methylphenol (F6) (3.31 g, 10 mmol) instead of 2-[(5-methoxy-2-methoxymethoxybenzylidene)amino]-3-methylphenol (F4) in 62% (2.07 g): $^1$H-NMR (400 MHz, CDCl$_3$) δ2.66 (s, 3H), 3.58 (s, 3H), 3.95 (s, 3H), 3.97 (s, 3H), 5.28 (s, 2H), 6.84 (s, 1H), 7.12 (d, 1H, J=8.0 Hz), 7.21 (t, 1H, J=8.0 Hz), 7.39 (d, 1H, J=8.0 Hz), 7.63 (s, 1H).

Example 17

Production of 2-(2,5-dimethoxyphenyl)-4-methylbenzoxazole (F10)

2-(2,5-dimethoxyphenyl)-4-methylbenzoxazole (F10) was prepared in a similar manner for the preparation of 2-(5-methoxy-2-methoxymethoxyphenyl)-4-methylbenzoxazole (F8) by using 2-[(2,5-dimethoxybenzylidene)amino]-3-methylphenol (F7) (5.43 g, 20 mmol) instead of 2-[(5- methoxy-2-methoxymethoxybenzylidene)amino]-3-methylphenol (F4) in 85% (4.55 g): $^1$H-NMR (500 MHz, CDCl$_3$) δ3.53 (s, 3H), 5.24 (s, 3H), 7.17 (d, H, J=9.0 Hz), 7.35 (d, 1H, J=9.0 Hz), 10.52 (s, 1H).

Example 18

Production of 2-(4-methoxymethoxyphenyl)-4-methylbenzoxazole (F11)

2-(4-methoxymethoxyphenyl)-4-methylbenzoxazole (F11) was prepared in a similar manner for the preparation of 2-(5-methoxy-2-methoxymethoxyphenyl)-4-methylbenzoxazole (F8) by using 2-[(4-methoxymethoxybenzylidene)amino]-3-methylphenol (F7) (5.43 g, 20 mmol) instead of 2-[(5-methoxy-2-methoxymethoxybenzylidene)amino]-3-methylphenol (F4) in 92% (4.92 g): $^1$H-NMR (500 MHz, CDCl$_3$) δ3.53 (s, 3H), 5.24 (s, 3H), 7.17 (d, 1H, J=9.0 Hz), 7.35 (d, 1H, J=9.0 Hz), 10.52 (s, 1H).

Example 19

Production of 4-bromomethyl-2-(5-methoxy-2-methoxymethoxyphenyl)benzoxazole (F2)

A mixture of 2-(5-methoxy-2-methoxymethoxyphenyl)-4-methylbenzoxazole (F8) (1.78 g, 5.95 mmol), N-bromosuccinimide (1.01 g, 5.95 mmol), and AIBN (82 mg, 0.5 mmol) in CCl$_4$ (100 mL) was refluxed for 15 h under dry N$_2$ gas flowing. The reaction mixture was cooled to 0° C., the precipitation was removed by filtration maintaining the temperature. After the solvent was evaporated, the residue was washed with small amount of ethanol several times to afford a pinkish solid (1.72 g, 76%). $^1$H-NMR (500 MHz, CDCl$_3$) δ3.57 (s, 3H), 3.88 (s, 3H), 4.96 (s, 2H), 5.27 (s, 2H), 7.05 (dd, 1H, J=8.5, 3.0 Hz), 7.22 (d, 1H, J=8.5 Hz), 7.34 (t, 1H, J=8.0 Hz), 7.42 (d, 1H, J=8.0 Hz), 7.54 (d, 1H, J=8.0 Hz), 7.66 (d, 1H, J=3.0 Hz).

Example 20

Production of 4-bromomethyl-2-(4,5-dimethoxy-2-methoxymethoxyphenyl)benzoxazole (F13)

4-bromomethyl-2-(4,5-dimethoxy-2-methoxymethoxyphenyl)benzoxazole (F13) was prepared in a similar manner for the preparation of 4-bromomethyl-2-(5-methoxy-2-methoxymethoxyphenyl)benzoxazole (F12) by using 2-(4,5-dimethoxy-2-methoxymethoxyphenyl)-4-methylbenzoxazole (F9) (1.39 g, 4.23 mmol) instead of 2-(5-methoxy-2-methoxymethoxyphenyl)-4-methylbenzoxazole (F8) in 66% (1.14 g): $^1$H-NMR (500 MHz, CDCl$_3$) δ3.60 (s, 3H), 3.97 (s, 3H), 3.99 (s, 3H), 4.96 (s, 2H), 5.31 (s, 2H), 6.85 (s, 1H), 7.30 (t, 1H, J=8.0 Hz), 7.40 (d, 1H, J=8.0 Hz), 7.51 (d, 1H, J=8.0 Hz), 7.66 (s, 1H).

Example 21

Production of 4-bromomethyl-2-(2,5-dimethoxyphenyl)benzoxazole (F14)

4-bromomethyl-2-(2,5-dimethoxyphenyl)benzoxazole (F14) was prepared in a similar manner for the preparation of 4-bromomethyl-2-(5-methoxy-2-methoxymethoxyphenyl)benzoxazole (F12) by using 2-(2,5-dimethoxyphenyl)-4-methylbenzoxazole (F10) (4.55 g, 16.9 mmol) instead of 2-(5-methoxy-2-methoxymethoxyphenyl)-4-methylbenzoxazole (F8) in 56% (3.30 g): $^1$H-NMR (500 MHz, CDCl$_3$) δ3.60 (s, 3H), 3.97 (s, 3H), 3.99 (s, 3H), 4.96 (s, 2H), 5.31 (s, 2H), 6.85 (s, 1H), 7.30 (t, 1H, J=8.0 Hz), 7.40 (d, 1H, J=8.0 Hz), 7.51 (d, 1H, J=8.0 Hz), 7.66 (s, 1H).

Example 22

Production of 4-bromomethyl-2-(4-methoxymethoxyphenyl)benzoxazole (F15)

4-bromomethyl-2-(4-methoxymethoxyphenyl)benzoxazole (F15) was prepared in a similar manner for the preparation of 4-bromomethyl-2-(5-methoxy-2-methoxymethoxyphenyl)benzoxazole (F12) by using 2-(4-methoxymethoxyphenyl)-4-methylbenzoxazole (F11) (4.04 g, 15 mmol) instead of 2-(5-methoxy-2-methoxymethoxyphenyl)-4-methylbenzoxazole (F8) in 80% (4.16 g): $^1$H-NMR (500 MHz, CDCl$_3$) δ3.60 (s, 3H), 3.97 (s, 3H), 3.99 (s, 3H), 4.96 (s, 2H), 5.31 (s, 2H), 6.85 (s, 1H), 7.30 (t, 1H, J=8.0 Hz), 7.40 (d, 1H, J=8.0 Hz), 7.51 (d, 1H, J=8.0 Hz), 7.66 (s, 1H).

Example 23

Production of 2-(5-methoxy-2-methoxymethoxyphenyl)-4-(2-pyridylmethyl)aminomethylbenzoxazole (F16)

A mixture of 4-bromomethyl-2-(5-methoxy-2-methoxymethoxyphenyl)benzoxazole (F12) (567 mg, 1.5 mmol), 2-(aminomethyl)pyridine (1.08 g, 10 mmol), and Na$_2$CO$_3$ (excess) in CH$_3$CN (30 mL) was stirred overnight at room temperature. After filtration of the reaction mixture, the filtrate was concentrated in vacuo. Water (20 mL) was added to the residue, which was extracted with CHCl$_3$ (20 mL) three times. The combined organic layer was washed with brine and water, dried over MgSO$_4$, and evaporated. The resulting oily material was purified by silica gel column chromatography (CHCl$_3$-ethyl acetate) to afford the objective compound as a pale yellow oil (386 mg, 63%). $^1$H-NMR (400 MHz, CDCl$_3$) δ3.52 (s, 3H), 3.87 (s, 3H), 4.01 (s, 2H), 4.30 (s, 2H), 5.23 (s, 2H), 7.02 (dd, 1H, J=9.2, 1.2 Hz), 7.15 (dd, 1H, J=7.6, 4.4 Hz), 7.21 (d, 1H, J=9.2 Hz), 7.29-7.36 (m, 2H), 7.41 (d, 1H, J=7.6 Hz), 7.49 (d, 1H, J=7.6 Hz), 7.62-7.65 (m, 2H), 8.55 (d, 1H, J=4.4 Hz).

Example 24

Production of 2-(5-methoxy-2-methoxymethoxyphenyl)-4-N-(2-pyridylmethyl)-N-methyl-aminomethylbenzoxazole (F17)

A mixture of 4-bromomethyl-2-(5-methoxy-2-methoxymethoxyphenyl)benzoxazole (F12) (567 mg, 1.5 mmol), N-methyl-N-(2-pyridylmethyl)amine (183 mg, 1.5 mmol), and Na$_2$CO$_3$ (excess) in CH$_3$CN (30 mL) was stirred overnight at room temperature. After filtration of the reaction mixture, the filtrate was concentrated in vacuo. Water (20 mL) was added to the residue, which was extracted with CHCl$_3$ (20 mL) three times. The combined organic layer was washed with brine and water, dried over MgSO$_4$, and evaporated. The resulting oily material was purified by silica gel column chromatography (CHCl$_3$-ethyl acetate) to afford the objective compound as a pale yellow oil (386 mg, 63%). $^1$H-NMR (400 MHz, CDCl$_3$) δ3.52 (s, 3H), 3.87 (s, 3H), 4.01 (s, 2H), 4.30 (s, 2H), 5.23 (s, 2H), 7.02 (dd, 1H, J=9.2, 1.2 Hz), 7.15 (dd, 1H, J=7.6, 4.4 Hz), 7.21 (d, 1H, J=9.2 Hz), 7.29-7.36 (m, 2H), 7.41 (d, 1H, J=7.6 Hz), 7.49 (d, 1H, J=7.6 Hz), 7.62-7.65 (m, 2H), 8.55 (d, 1H, J=4.4 Hz).

Example 25

Production of 4-bis(2-pyridylmethyl)aminomethyl-2-(5-methoxy-2-methoxymethoxyphenyl)benzoxazole (F18)

4-bis(2-pyridylmethyl)aminomethyl-2-(5-methoxy-2-methoxymethoxyphenyl)-benzoxazole (F18) was prepared in a similar manner for the preparation of 2-(5-methoxy-2-methoxymethoxyphenyl)-4-N-(2-pyridylmethyl)-N-methyl-aminomethylbenzoxazole (F17) using di(2-picolyl)amine (317 mg, 1.59 mmol) instead of N-methyl-N-(2-pyridylmethyl)amine in 92% (730 mg): $^1$H-NMR (500 MHz, CDCl$_3$) δ3.53 (s, 3H), 3.87 (s, 3H), 3.94 (s, 4H), 4.23 (s, 2H), 5.24 (s, 2H), 7.03 (dd, 1H, J=9.0, 3.5 Hz), 7.12 (dd, 1H, J=7.5, 5.0 Hz), 7.22 (d, 1H, J=9.0 Hz), 7.34 (t, 1H, J=7.5 Hz), 7.48 (d. 1H, J=7.5 Hz), 7.56 (d, 1H, J=7.5 Hz), 7.64-7.68 (m, 3H), 7.75 (d, 2H, J=7.5 Hz), 8.52 (d, 2H, J=5.0 Hz).

Example 26

Production of 2-(4,5-dimethoxy-2-methoxymethoxyphenyl)-4-(2-pyridylmethyl)aminomethylbenzoxazole (F19)

2-(4,5-dimethoxy-2-hydroxyphenyl)-4-(2-pyridylmethyl)aminomethyl-benzoxazole (F19) was prepared in a similar manner for the preparation of 2-(5-methoxy-2-methoxymethoxyphenyl)-4-(2-pyridylmethyl)aminomethylbenzoxazole (F16) using 4-bromomethyl-2-(4,5-dimethoxy-2-methoxymethoxyphenyl)benzoxazole (F13) (612 mg, 1.59 mmol) instead of 4-bromomethyl-2-(5-methoxy-2-methoxymethoxyphenyl)benzoxazole (F12) in 17% (112 mg); $^1$H-NMR (500 MHz, CDCl$_3$) δ3.56 (s, 3H), 3.95 (s, 3H), 3.97 (s, 3H), 4.02 (s, 2H), 4.30 (s, 2H), 5.27 (s, 2H), 6.85 (s, 1H), 7.15 (dd, 1H, J=7.5, 5.0 Hz), 7.28 (t, 1H, J=7.5 Hz), 7.33 (d, 1H, J=7.5 Hz), 7.42 (d, 1H, J=7.5 Hz), 7.47 (d, 1H, J=7.5 Hz), 7.64 (m, 2H), 8.55 (d, 1H, J=5.0 Hz).

Example 27

Production of 2-(4,5-dimethoxy-2-methoxymethoxyphenyl)-4-N-(2-pyridylmethyl)-N-methyl-aminomethylbenzoxazole (F20)

2-(4,5-dimethoxy-2-methoymethoxyphenyl)-4-N-(2-pyridylmethyl)-N-methyl-aminomethylbenzoxazole (F20) was prepared in a similar manner for the preparation of 2-(5-methoxy-2-methoxymethoxyphenyl)-4-N-(2-pyridylmethyl)-N-methyl-aminomethylbenzoxazole (F17) using 4-bromomethyl-2-(4,5-dimethoxy-2-methoxymethoxyphenyl)benzoxazole (F13) (408 mg, 1.0 mmol) instead of 4-bromomethyl-2-(5-methoxy-2-methoxymethoxyphenyl)benzoxazole (F12) in 71% (317 mg); $^1$H-NMR (500 MHz, CDCl$_3$) δ2.35 (s, 3H), 3.58 (s, 3H), 3.84 (s, 2H), 3.96 (s, 3H), 3.98 (s, 3H), 4.13 (s, 2H), 5.28 (s, 2H), 6.85 (s, 1H), 7.15 (dd, 1H, J=7.5, 5.0 Hz), 7.32 (t, 1H, J=8.0 Hz), 7.46-7.50 (m, 2H), 7.61-7.69 (m, 3H), 8.55 (d, 1H, J=5.0 Hz).

Example 28

Production of 4-bis(2-pyridylmethyl)aminomethyl-2-(4-methoxymethoxyphenyl)benzoxazole (F21)

4-bis(2-pyridylmethyl)aminomethyl-2-(4-methoxymethoxyphenyl)benzoxazole (F21) was prepared in a similar manner for the preparation of 4-bis(2-pyridylmethyl)aminomethyl-2-(5-methoxy-2-methoxymethoxyphenyl) benzoxazole (F18) using 4-bromomethyl-2-(4-methoxymethoxyphenyl)benzoxazole (F15) (552 mg, 1.5 mmol) instead of 4-bromomethyl-2-(5-methoxy-2-methoxymethoxyphenyl)benzoxazole (F12) in 98% (704 mg); $^1$H-NMR (400 MHz, CDCl$_3$) δ3.52 (s, 3H), 3.93 (s, 4H), 4.19 (s, 2H), 5.26 (s, 2H), 7.11-7.18 (m, 4H), 7.29 (t, 1H, J=8.0 Hz), 7.44 (d, 1H, J=8.0 Hz), 7.51 (d, 1H, J=8.0 Hz), 7.66 (d, 2H, J=7.6 Hz), 7.78 (d, 2H, J=7.6 Hz), 8.19 (d, 2H, J=9.2 Hz), 8.55 (d, 2H, J=5.0 Hz).

Example 29

Production of 4-bis(2-pyridylmethyl)aminomethyl-2-(2,5-dimethoxyphenyl)benzoxazole (F22)

4-bis(2-pyridylmethyl)aminomethyl-2-(2,5-dimethoxyphenyl)benzoxazole (F22) was prepared in a similar manner for the preparation of 4-bis(2-pyridylmethyl)aminomethyl-2-(5-methoxy-2-methoxymethoxyphenyl) benzoxazole (F18) using 4-bromomethyl-2-(2,5-dimethoxyphenyl)benzoxazole (F14) (522 mg, 1.5 mmol) instead of 4-bromomethyl-2-(5-methoxy-2-methoxymethoxyphenyl)benzoxazole (F12) in 91% (640 mg); $^1$H-NMR (400 MHz, CDCl$_3$) δ3.88 (s, 4H), 3.95 (s, 6H), 4.23 (s, 2H), 7.01-7.07 (m, 2H), 7.13 (dd, 2H, J=8.0, 5.0 Hz), 7.34 (t, 1H, J=7.5 Hz), 7.49 (d, 1H, J=7.5 Hz), 7.57 (d, 1H, J=7.5 Hz), 7.64-7.68 (m, 3H), 7.80 (d, 2H, J=8.0 Hz), 8.52 (d, 2H, J=5.0 Hz).

Example 30

Production of 2-(5-methoxy-2-hydroxyphenyl)-4-(2-pyridylmethyl)aminomethyl-benzoxazole (F23)

A mixture of 2-(5-methoxy-2-methoxymethoxyphenyl)-4-(2-pyridylmethyl)aminomethyl-benzoxazole (F16) (283 mg, 0.70 mmol) and p-toluenesulfonic acid monohydrate (532 mg, 2.8 mmol) in methanol (20 mL) was stirred overnight at room temperature. After the solvent was removed by evaporation, ethyl acetate (20 mL) was added to the resulting residue, neutralized by Na$_2$CO$_3$, washed with brine and water, dried over MgSO$_4$, and concentrated in vacuo. The residue was recrystallized from hot ethanol/hexane to afford the objective compound as a pale yellow crystal (244 mg, 96%); $^1$H-NMR (500 MHz, CDCl$_3$) δ3.86 (s, 3H), 4.01 (s, 2H), 4.21 (s, 2H), 7.05 (br s, 2H), 7.17 (dd, 1H, J=7.5, 4.5 Hz), 7.33-7.37 (m, 2H), 7.41 (d, 1H, J=7.5 Hz), 7.48-7.51 (m, 2H), 7.66 (t, 1H, J=7.5 Hz), 8.59 (d, 1H, J=4.5 Hz), 11.00 (s, 1H).

Example 31

Production of 2-(5-methoxy-2-hydroxyphenyl)-4-N-(2-pyridylmethyl)-N-methyl-aminomethylbenzoxazole (F24)

2-(5-methoxy-2-hydroxyphenyl)-4-N-(2-pyridylmethyl)-N-methyl-aminomethyl-benzoxazole (F24) was prepared in a similar manner for the preparation of 2-(5-methoxy-2-hydroxyphenyl)-4-(2-pyridylmethyl)aminomethyl-benzoxazole (F23) using 2-(5-methoxy-2-methoxymethoxyphenyl)-4-N-(2-pyridylmethyl)-N-methyl-aminomethylbenzoxazole (F17) (209 mg, 0.5 mmol) instead of 2-(5-methoxy-2-methoxymethoxyphenyl)-4-(2-pyridylmethyl)aminomethyl-benzoxazole (16) in 93% (173 mg); $^1$H-NMR (500 MHz, CDCl$_3$) δ2.32 (s, 3H), 3.81 (s, 2H), 3.87 (s, 3H), 4.01 (s, 2H), 7.05 (s, 2H), 7.17 (dd, 1H, J=7.5, 4.5 Hz), 7.34 (t, 1H, J=7.5 Hz), 7.46-7.52 (m, 3H), 7.58 (d, 1H, J=7.5 Hz), 7.71 (t, 1H, J=7.5 Hz), 8.56 (d, 1H, J=4.5 Hz), 11.13 (s, 1H).

Example 32

Production of 4-bis(2-pyridylmethyl)aminomethyl-2-(2-hydroxy-5-methoxyphenyl)benzoxazole (F25)

4-bis(2-pyridylmethyl)aminomethyl-2-(2-hydroxy-5-methoxyphenyl)benzoxazole (F25) was prepared in a similar manner for the preparation of 2-(5-methoxy-2-hydroxyphenyl)-4-(2-pyridylmethyl)aminomethylbenzoxazole (F23) using 4-bis(2-pyridylmethyl)aminomethyl-2-(5-methoxy-2-methoxymethoxyphenyl)benzoxazole (F17) (136 mg, 0.275 mmol) instead of 2-(5-methoxy-2-methoxymethoxyphenyl)-4-(2-pyridylmethyl)aminomethylbenzoxazole (F16) in 98% (122 mg); $^1$H-NMR (500 MHz, CDCl$_3$) δ3.87 (s, 3H), 3.89 (s, 4H), 4.12 (s, 2H), 7.06 (br s, 2H), 7.14 (dd, 1H, J=7.5, 4.0 Hz), 7.35 (t, 1H, J=8.0 Hz), 7.49-7.53 (m, 3H), 7.64-7.70 (m, 4H), 8.52 (d, 2H, J=4.0 Hz), 11.06 (s, 1H).

Example 33

Production of 2-(4,5-dimethoxy-2-hydroxyphenyl)-4-(2-pyridylmethyl)aminomethylbenzoxazole (F26)

2-(4,5-dimethoxy-2-hydroxyphenyl)-4-(2-pyridylmethyl)aminomethyl-benzoxazole (F26) was prepared in a similar manner for the preparation of 2-(5-methoxy-2-hydroxyphenyl)-4-(2-pyridylmethyl)aminomethylbenzoxazole (F23) using 2-(4,5-dimethoxy-2-methoxymethoxyphenyl)-4-(2-pyridylmethyl)aminomethylbenzoxazole (F17) (100 mg, 0.23 mmol) instead of 2-(5-methoxy-2-methoxymethoxyphenyl)-4-(2-pyridylmethyl)aminomethylbenzoxazole (F16) in 92% (83 mg); $^1$H-NMR (500 MHz, CDCl$_3$) δ3.95 (s, 3H), 3.96 (s, 3H), 4.01 (s, 2H), 4.21 (s, 2H), 6.66 (s, 1H), 7.17 (dd, 1H, J=7.5, 5.0 Hz), 7.31 (t, 1H, J=8.0 Hz), 7.37-7.40 (m, 2H), 7.41 (s, 1H), 7.48 (d, 1H, J=8.0 Hz), 7.67 (t, 1H, J=7.5 Hz), 8.66 (d, 2H, J=5.0 Hz), 11.27 (s, 1H).

Example 34

Production of 2-(4,5-dimethoxy-2-hydroxyphenyl)-4-N-(2-pyridylmethyl)-N-methyl-aminomethylbenzoxazole (F27)

2-(4,5-dimethoxy-2-hydroxyphenyl)-4-N-(2-pyridylmethyl)-N-methyl-aminomethylbenzoxazole (F27) was prepared in a similar manner for the preparation of 2-(5-methoxy-2-hydroxyphenyl)-4-(2-pyridylmethyl)aminomethylbenzoxazole (F23) using 2-(4,5-dimethoxy-2-methoxymethoxyphenyl)-4-N-(2-pyridylmethyl)-N-methyl-aminomethylbenzoxazole (F20) (270 mg, 0.6 mmol) instead of 2-(5-methoxy-2-methoxymethoxyphenyl)-4-(2-pyridylmethyl)aminomethylbenzoxazole (F16) in 94% (221 mg); $^1$H-NMR (500 MHz, CDCl$_3$) δ2.33 (s, 3H), 3.81 (s, 2H), 3.95 (s, 3H), 3.96 (s, 3H), 3.99 (s, 2H), 6.65 (s, 1H), 7.17 (dd, 1H, J=7.5, 4.5 Hz), 7.31 (t, 1H, J=8.0 Hz), 7.41 (s, 1H), 7.44-7.48 (m, 2H), 7.59 (d, 1H, J=8.0 Hz), 7.71 (t, 1H, J=7.5 Hz), 8.56 (d, 2H, J=4.5 Hz), 11.39 (s, 1H).

Example 35

Production of 4-bis(2-pyridylmethyl)aminomethyl-2-(4-hydroxyphenyl)benzoxazole (F28)

4-bis(2-pyridylmethyl)aminomethyl-2-(4-hydroxyphenyl)benzoxazole (F28) was prepared in a similar manner for the preparation of 2-(5-methoxy-2-hydroxyphenyl)-4-(2-pyridylmethyl)aminomethylbenzoxazole (F23) using 4-bis(2-pyridylmethyl)aminomethyl-2-(4-methoxymethoxyphenyl)benzoxazole (F21) (686 mg, 1.47 mmol) instead of 2-(5-methoxy-2-methoxymethoxyphenyl)-4-(2-pyridylmethyl)aminomethylbenzoxazole (F16) in 81% (500 mg); $^1$H-NMR (500 MHz, CDCl$_3$) δ3.97 (s, 4H), 4.18 (s, 2H), 6.88 (d, 2H, J=9.0 Hz), 7.16 (dd, 2H, J=8.0, 4.5 Hz), 7.24 (t, 1H, J=8.0 Hz), 7.40 (d, 1H, J=8.0 Hz), 7.45 (d, 2H, J=8.0 Hz), 7.69 (t, 2H, J=8.0 Hz), 7.79 (d, 2H, J=8.0 Hz), 8.00 (d, 2H, J=9.0 Hz), 7.24 (d, 2H, J=4.5 Hz).

Example 36

Production of zinc complex using Formula 25. To a solution of 4-bis(2-pyridylmethyl)aminomethyl-2-(2-hydroxy-5-methoxyphenyl)benzoxazole (F25) (133 mg, 0.27 mmol) and triethylamine (38 μL, 0.27 mmol) in methanol (5 mL) was added ZnCl$_2$ (36.5 mg, 0.27 mmol), and the mixture was stirred for 2 h. KPF$_6$ (184 mg, 1.0 mmol) was then added into the solution and the mixture was stirred for an additional 2 h. The resulting solution was concentrated in vacuo, and the residue was dissolved in small amount of methanol that was poured into ether (50 mL). The precipitate was collected by filtration and washed with water to afford yellow powder (135 mg, 75%). Single crystals (yellow cubic) for X-ray structure determination were obtained by recrystallization from methanol/ether diffusion.

Example 37

Production of zinc complex using Formula 24. To a solution of 2-(5-methoxy-2-hydroxyphenyl)-4-N-(2-pyridylmethyl)-N-methyl-aminomethyl-benzoxazole (F24) (75 mg, 0.2 mmol) and triethylamine (28 μL, 0.2 mmol) in methanol (5 mL) was added ZnCl$_2$ (27 mg, 0.2 mmol), and the mixture was stirred for 3 h. The reaction mixture was subsequently poured into ether (50 mL) and the precipitate was collected by filtration (385 mg, 81%). Single crystals (yellow cubic) for X-ray structure determination were obtained by recrystallization from methanol/ether diffusion.

While the principles of this invention have been described in connection with specific embodiments, it should be understood that these descriptions are added only by way of example and are not intended to limit, in any way, the scope of this invention. For instance, compounds of the present invention can be extended to include a range of analogous fused heterocyclic compounds (e.g., benzthiazoles, etc.) using straightforward modifications of the synthetic techniques described herein, such techniques as would be understood by those skilled in the art made aware of this invention. Likewise, substitution at the 4-position of the fused heterocyclic system can vary, limited only by desired interaction with Zn$^{+2}$ metal ion and/or solvent solubility. Regardless of the compound or substitution, various imaging or spectroscopic techniques, known in the art, can be used in conjunction therewith.

We claim:

1. A fluorescent compound of a formula

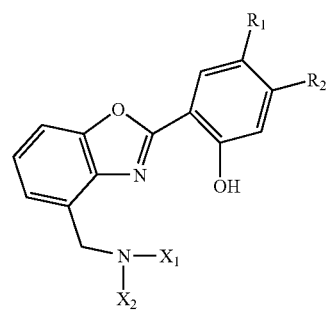

wherein R$_1$ and R$_2$ are independently selected from hydrogen, hydroxy, alkyl and alkoxy; and X$_1$ is (2-pyridinylalkyl); and X$_2$ is (2-pyridinylalkyl).

* * * * *

UNITED STATES PATENT AND TRADEMARK OFFICE
CERTIFICATE OF CORRECTION

PATENT NO.        : 7,262,301 B1
APPLICATION NO.   : 11/519367
DATED             : August 28, 2007
INVENTOR(S)       : Thomas V. O'Halloran et al.

It is certified that error appears in the above-identified patent and that said Letters Patent is hereby corrected as shown below:

Col. 1, Line 11: "Grant Nos. DK52627 and GM38784 from the National Institutes of Health and the National Science Foundation, respectively,"

should be --Grant Nos. DK52627, GM38784 from the National Institutes of Health and CHE9810378 from the National Science Foundation, respectively--

Col. 7, Lines 34-35: "(2-pyridlmethyl)" should be --(2-pyridylmethyl)--

Col. 9, Line 38: "pK," should be --$pK_1$--

Col. 11, Line 3: "Fe+" should be --$Fe^2+$--

Col. 15, Line 25: "(F2)" should be --(F12)--

Signed and Sealed this

First Day of April, 2008

JON W. DUDAS
*Director of the United States Patent and Trademark Office*